US006228366B1

(12) United States Patent
Ferrer et al.

(10) Patent No.: US 6,228,366 B1
(45) Date of Patent: May 8, 2001

(54) **WATER-SOLUBLE FRACTIONS OF *PHLEBODIUM DECUMANUM* AND ITS USE AS NUTRITIONAL SUPPLEMENT IN AIDS AND CANCER PATIENTS**

(75) Inventors: Miguel Yesares Ferrer, La Zubia-Granada (ES); Jorge A. Mendoza Medina; Giovanna Marisol Ruiz Caceres, both of El Picacho-Tegucigalpa (HN); Antonio Alcaide Garcia, Madrid; Miguel Enrique Yesares Morillas, Granada, both of (ES)

(73) Assignee: Helsint, S.A.L., Granada (ES)

( * ) Notice: Subject to any disclaimer, the term of this patent is extended or adjusted under 35 U.S.C. 154(b) by 0 days.

(21) Appl. No.: 09/269,497
(22) PCT Filed: Jul. 29, 1998
(86) PCT No.: PCT/ES98/00220
§ 371 Date: Mar. 29, 1999
§ 102(e) Date: Mar. 29, 1999
(87) PCT Pub. No.: WO99/06058
PCT Pub. Date: Feb. 11, 1999
(51) Int. Cl.$^7$ .............................. A61K 35/78; A23L 1/30
(52) U.S. Cl. ..................... 424/195.1; 424/405; 426/648; 426/655
(58) Field of Search ................................ 424/195.1, 405; 426/648, 655

(56) References Cited

U.S. PATENT DOCUMENTS

| | | | |
|---|---|---|---|
| 3,395,223 | * | 7/1968 | Berger et al. ...................... 424/195.1 |
| 4,206,222 | * | 6/1980 | Valetas .................................. 514/460 |
| 5,601,829 | * | 2/1997 | Quintanilla Almagro et al. ....... 424/195.1 |
| 5,614,197 | * | 3/1997 | Pathak et al. ...................... 424/195.1 |

FOREIGN PATENT DOCUMENTS

| | | | |
|---|---|---|---|
| 0503208 | * | 9/1992 | (EP) . |
| 2022094 | * | 1/1980 | (GB) . |
| 2075834 | * | 11/1981 | (GB) . |

OTHER PUBLICATIONS

Horvath, A. Nature, vol. 214, pp. 1256–1258, 1967.*

* cited by examiner

Primary Examiner—Christopher R. Tate
(74) Attorney, Agent, or Firm—Michaelson & Wallace; Peter L. Michaelson; Edward M. Fink

(57) ABSTRACT

A purified and standardized water-soluble fraction, prepared from the leaves of a variety of *Phlebodium decumanum* and identified as EXPLY-37, is adequate for the manufacturing of formulations, useful as nutritional supplements of general application, and more particularly, in patients suffering from general weakness and cachexia, such as AIDS an cancer patients. The formulations can contain, optionally, powdered *Phlebodium decumanum* rhizome and/or *Phlebodium decumanum* rhizome extract, together with the appropriate excipients for preparing said formulation as powders, capsules and syrups.

18 Claims, No Drawings

WATER-SOLUBLE FRACTIONS OF *PHLEBODIUM DECUMANUM* AND ITS USE AS NUTRITIONAL SUPPLEMENT IN AIDS AND CANCER PATIENTS

FIELD OF THE INVENTION

This invention relates to a purified and standardized water-soluble fraction obtained from the leaves of a cultivated variety of *Phlebodium decumanum*, identified as EXPLY-37, to formulations containing it and to their use as nutritional supplements of general application and particularly, in patients suffering from general weakness and cachectic syndrome, as AIDS and cancer patients. Such formulations can also be used in combination with anti-retroviral drugs in AIDS patients and with conventional anticancer treatments (surgery and/or radio-and chemotherapy) in order to improve the efficacy and to reduce the undesired effects of such treatments. The formulations are also useful in the recovery of patients under those treatments.

BACKGROUND OF THE INVENTION

Cachexia is a complex syndrome characterized by appetite and body weight loss, general weakness, anemia and asthenia. This syndrome is associated to a metabolic dysbalance and shown by weight loss and generalized wasting: the organism is unable to maintain the adequate energy supply and spends its own lipid store and muscle protein.

It is accepted that a high percentage (50–90%) of HIV infected patients suffer from some kind of malnutrition. This disturbance can be attributed to alterations in the intake, absorption and metabolism of foods [C. Fields-Gardner, Nutr.Clin. Pract. 1995, 10(5), 167–176.] Severe weight loss is closely related to the mortality increase in AIDS patients. It may be related, on the other hand, to some kind of gastrointestinal pathology, anorexia, systemic infections and can appear in patients with advanced disease and CD4+ count lower than 100 [D. P. Kotler, AIDS Res. Hum. Retroviruses 1994, 10(8), 930–934]

Wasting syndrome associated to HIV infection is characterized by progressive weight loss and increasing weakness, frequently associated to fever and diarrhea. The causes of these alterations are complexes, multifactorial and seem to be related to inadequate diets, malabsorption phenomena, metabolic dysbalance and activity of some cytokines such as tumor necrosis factor (TNF), IL-1, IL-6 and $\alpha$-IFN [S. E. Weinroth et al. Infect. Agents Dis. 1995, 4,76–94]. P. Kelly et al. [Q.S. Med. 1996, 89 (II), 831–837] found a relationship between the severity of cachexia in a group of African males and the high cytokine activity, specially high concentrations of sTNF55, although no correlation could be established with either oesophagic candidiasis or any intestinal opportunistic infection.

The relationship between wasting syndrome and low blood levels of testosterone has been demonstrated in male AIDS patients. Special diets, testosterone, nandrolone [J. Gold et al. 1996, 10 (7), 108–112] and growth hormone [M. Shambelan et al. Ann. Inter. Med. 1996, 125 (11), 873–882] have been used for the treatment of cachexia in AIDS patients.

The relationships between nutrition, HIV infection and immune system [J. M. Hoyt et al., II. Assoc. Nurses AIDS care 1991, 2 (3), 16–28,] and the role of certain cytokines in the wasting syndrome in AIDS patients, can be considered as the basis for new treatments involving the use of immunomodulators. The use of thalidomide, an immunomodulating drug, in the treatment of the wasting syndrome associated to AIDS has recently been published [G. Reyes-Teran et al., AIDS, 1996, 10, 1501–1507].

On the other hand, cachexia is also associated to the high mortality rate in cancer patients, this rate being estimated by some authors as 30–70%. Many cancer patients die after continuous weight loss and generalized weakness. Oncology patients with associated cachexia have a negative prognostic as the possibilities of effective chemoterapeutic treatments are substantially reduced. Consequently, an effective treatment of cachexia should improve the general condition of the patient: more effective chemotherapy, better quality of life and more favorable prognosis of the disease could be achieved.

However, all the approaches for slowing down or reverting cachexia have been focused on the improvement of nutritional supply through special diets and regimen without positive results.

Recent publications are now stressing the relationships between the high levels of certain pro-inflammatory citokynes and cancer cachexia: TNF$\alpha$, IL-1, IL-6 and IFN gamma [P. Elliot et al., Drug &. Market Development 1989, 9, 26–18.] This dysfunction of the immune system, together with reduction in the NK cell activity and plasma levels of cystine and glutamine, accompanied of urea overproduction, shown in different pathologies, is extremely important in the induction and progression of cachexia in cancer patients. Although the induction mechanism by such cytokines is unknown, antagonizing their effects by using inmunomodulators is one of the most updated approaches to revert cachexia.

It is obviously necessary to develop new ways to stop or revert the cachetic syndrome in order to improve the quality of life and to enhance the efficacy of basic treatments.

The fern known for years as *Polypodium leucotomos* has historically been used by the Honduran natives, as infusions of leaves and rhizomes, for the treatment of malign tumors, rheumatoid arthritis and psoriasis. Horvath et al. [Nature, 1967, 214, 1256–1258] showed both the in vitro and in vivo antitumor effect of an aqueous extract of the fern. Later, a water soluble fraction from the leaves of *Polypodium leucotomos* has been widely studied. Its inmunomodulator/inmunosuppresor profile and its antioxidant and anti-free radical properties have been described [M. D. Fernandez & al. 1$^{st}$ World Congress on Medicinal and Aromatic Plant for Human Welfare, Maastricht, 1992; J. Rayward et al., 2$^{nd}$ International Congress on Biological Response Modifiers, San Diego, USA, S. Gonzalez & al., Photodermatol, Photoimmunol, Photomed, 1996, 12,45]

The use of extracts from the genus Polypodium, and more specifically from *Polypodium leucotomos*, as antioxidants and photoprotectants has been claimed in the patent PCT/US 96/01808 by Pathak et al. (1996).

The present invention provides a water soluble fraction obtained from the leaves of a cultivated variety of *Phlebodium decumanum*, purified and standardized, identified as EXPLY-37, its production and its use in the manufacturing of formulations useful as nutritional supplements. The plant material from which the water soluble extract employed herein, identified as "EXPLY 37", is obtained from the leaves of a cultivated variety of Phlebodium decumanum found in the Yojoa Lake region of northern Honduras. In accordance with the provisions of 37 C.F.R. 1.802 this plant material has been deposited in an International Depositary Authority (IDA) established under the Budapest Treaty on the International Recognition of the Deposit of Microorganisms for the Purposes of Patent Procedure. This deposit was made by transmission of a number of spores of the variety of Phlebodium decumanum from which EXPLY 37 is extracted on Oct. 19, 2000 to the National Collection of Industrial and Marine Bacterial Ltd. (NCIMB), Aberdeen, Scotland (United Kingdom). The deposit was received on Oct. 16, 2000.

DESCRIPTION OF THE INVENTION

This invention is addressed, but not limited, to the manufacturing of a water-soluble fraction from the leaves of a cultivated variety of Phlebodium decumanum, purified and standardized, identified as EXPLY-37, to the preparation of EXPLY-37 formulations and to the use of these formulations as nutritional supplements in AIDS and cancer patients. The formulations can be used together with anti-retroviral drugs in AIDS patients and associated to conventional oncology treatments (surgery and/or radio-and chemotherapy), in order to improve the efficacy and reduce the side effects in the recovery of patients under those treatments.

1. Phlebodium decumanum

This Polypodiacee, belonging to the Subgenus Phlebodium, within the Genus Polypodium, is organically cultivated and processed in the facility near the Yojoa lake (Northern Honduras). This facility is owned by HELSINT S.A.L. (Spain) and exploited by Helechos International, Honduras, S.A. (HIH). The plant has been considered for years as Polypodium leucotomos but has been reclassified in 1992, according to the in situ studies carried out by Prof.Cirile Nelson, Director of the Herbario TEFH, Department of Biology, UNAH (Tegucigalpa, Honduras), Prof. Sinn Sandberg, Uppsala University, and Prof. Antonio Molina, from the Paul C. Stanley Herbario and the Escuela Agricola Panamericana. A full agreement has been reached on the new nomenclature. The relationships among the different Polypodium species have been furthermore reviewed by M. Väsange, Ph. Thesis, Uppsala University, 1996.

The lake Yojoa cultures are the only ones existing in the world where both ferns—Phlebodium decumanum and Polipodium leucotomos—, are cultivated.

2. Water-soluble Fractions of Phlebodium decumanum

EXPLY-37 is the tradename, property of HELSINT S.A.L. and applied to the Extract of Phlebodium decumanum from the Yojoa Lake. No 37 corresponds to the extraction method selected among those tested for the preparation of the extract from the leaves and is based on the methods disclosed in patents G B 2,024. 622 A, GB 2075, 834-A, ES 8902092 and more recently in WO 96/5139.

Sporulated leaves from Phlebodium decumanum, dried and ground, are delipidated by treatment with petroleum ether, methylene choride or mixtures petroleum ether/methylene chloride, then extracted with a mixture of methanol/water. An alternative method consists in the extraction with a mixture of methyl alcohol/water followed by delipidation of the extract with petroleum ether, methylene chloride or mixtures petroleum ether/methylene chloride.

By removing the methyl alcohol at reduced pressure the remaining water-soluble fraction is purified by passing it through a mixed ion-exchange column, treatment with active charcoal, sodium metabisulphyte and filtration.

The purified water-soluble fraction is concentrated until a batch-to-batch constant and reproducible composition within a narrow range. Example 1 describes a method for the preparation of a water-soluble fraction from the leaves of Phlebodium decumanum identified as EXPLY-37. A typical composition of EXPLY-37 is shown in Table 1.

The tradename EXPLY-37 has been applied by HELSINT S:A:L to distinguish the extract from the variety of Phlebodium decumanum cultivated in the lake Yojoa facility and to differentiate it from wild varieties of Phlebodium decumanum from other origins.

A water-soluble fraction, purified and standardized, can also be obtained from the rhizome by the following method: the rhizome, after removing all the villosities, is washed with an sterilizing solution and deionized water, dried, ground, and extracted with a mixture of methyl alcohol/water. After removal of the alcohol in the vacuum, the cloudy water-soluble fraction is treated with petroleum ether, methylene chloride or mixtures petroleum ether/methylene chloride to remove the remain lipids. The solution is clarified with active charcoal, treated with sodium metabisulphite, filtered and concentrated until a batch-to-batch constant and reproducible composition, within a narrow range. Example 2 describes a method for the preparation of a water-soluble fraction, or extract, from the rhizome of Phlebodium decumanum. A typical composition of such fraction is shown on TABLE 2.

3. Formulations Containing EXPLY-37 for Use by Oral Route

The invention provides formulations containing EXPLY-37 useful as nutritional supplements. These formulations may additionally contain rhizome and/or rhizome water-soluble fraction. The formulations, adequate for oral administration, can be solid or liquid and used as powders, soft or hard gelatine capsules or syrups.

3.1 Solid Formulations Containing EXPLY-37

3.1.a) Mixture Containing Powdered Rhizome of Phlebodiun decumanum and EXPLY-37

This preparation can be obtained by a method consisting of the following steps:

successive washings of the rhizome with water containing active chlorine, de-ionized water, ethyl alcohol and de-ionized water.

drying of the rhizome grinding of the rhizome and homogenization to a selected particle size incorporation of EXPLY-37 drying.

This mixture of EXPLY-37 and Phlebodium decumanum rhizome, ground and homogenized, can be used as a powder to fill hard gelatine capsules containing between 100 and 500 mg powder. The ratio [ground and homogenized rhizome: EXPLY-37] in the mixture is within the range 4:1 to 1.1.

3.1.b) Mixture Containing Powdered *Phlebodium decumanum* Rhizomes EXPLY-37 and *Phlebodium decumanum* Rhizome Extract This preparation can be obtained by a similar method to that summarised in 3.1.a), although different mixtures of EXPLY-37 and rhizome extract (50:50 to 95:5) can be added in different proportions. The solid mixture containing EXPLY-37, rhizome powder and rhizome extract of *Phlebodium decumanum*, prepared as a dry powder, can be used to fill hard gelatine capsules containing 100–500 mg solid powder. The relative proportions [EXPLY-37+rhizome extract]:[rhizome] can be in the range 4:1 to 1:1

3.2 Liquid Formulations Containing EXPLY-37

These formulations can be prepared as soft gelatine capsules and syrups.

3.2.a) Soft gelatine capsules containing EXPLY-37

The capsules con be filled by direct injection of diluted EXPLY-37 having the adequate viscosity. These capsules can contain 50–700 mg EXPLY-37.

3.2.b) Soft gelatine capsules containing EXPLY-37 and *Phlebodium decumanum* rhizome extract.

These capsules can be obtained by the following process:

Preparation of a homogeneous mixture containing EXPLY-37 and rhizome extract, the relative proportions ranging within the range (50:50 to 95:5)

Dilution of the mixture and injection in soft gelatine capsules. Total content [EXPLY-37+rhizome extract]: 50 to 750 mg.

3.2.c) Syrups containing EXPLY-37

A syrup can be prepared by homogenizing EXPLY-37 with the following components:

*Saccharum officinarum* liquid extract

*Glycyrrhiza glabra* liquid extract

Citric acid

Preferred formulations are those containing EXPLY-37 at a concentration of 50–500 mg/g.

3.2.d) Syrups containing mixtures of EXPLY-37+ *Phlebodium decumanum* rhizome extract [relative proportions (50:50) to (95:1)] and the following components:

*Sacharum officinarum* liquid extract

*Glycirrhiza glabra* liquid extract

Citric acid

Preferred formulations are those containing the mixture [EXPLY-37+rhizome extract] at a concentration of 50–500 mg/g.

3.2.e) Syrups containing EXPLY-37.

A different syrup can be prepared by the incorporation of EXPLY-37 to an aqueous solution containing the following excipients:

invert sugar sorbitol propylenglycol

Preferred formulations are those containing EXPLY-37 at a concentration of 20–500 mg/ml.

3.2.f) Syrups containing EXPLY-37 and *Phlebodium decumanum* rhizome extract.

Syrups can be prepared by incorporating a mixture containing various proportions [EXPLY-37: rhizome extract (50:50) to (95:5)] into an aqueous solution of following excipients:

invert sugar sorbitol propylenglycol

Preferred formulations are those containing 20–50 mg [EXPLY-37+rhizome extract/ml]

EXPLY-37 formulations provided in this invention are useful as nutritional supplement of general use.

These formulations are, particularly adequate for the treatment of malnutrition, body weight loss, generalized wasting and cachectic syndrome in AIDS patients [see the results obtained with AIDS patients: Clinical Results. I. AIDS patients with advanced HIV infection] and as a supplement to treatments with anti-retroviral drugs. The formulations are also useful for the treatment of cancer patients showing generalized weakness and cachectic impairment: as cachexia is slowing-down and reverting, a general improvement is obtained allowing a more efficacious application of the appropriate anti-cancer treatments. EXPLY-37 formulations can also be used as adjuvant in conventional oncology treatments (surgery and/or radio- and chemotherapy) and for the recovery of cancer patients, previously under such treatments [see the results obtained in cancer patients: Clinical Results. II. Treatment of cancer patients].

Treatment of cachectic syndrome in patients with advanced HIV infection is better performed by administration of the formulations provided in this invention at daily doses comprised between 1 and 5 g, expressed as EXPLY-37. Similar doses are adequate for the treatment of cachectic syndrome in cancer patients, as adjuvant in conventional anti-cancer treatments and in the recovery of cancer patients following to those treatments.

The following examples illustrate well the invention although they must not be considered limiting of the same.

EXAMPLE 1

Preparation of EXPLY-37 from *Phlebodium decumanum* Leaves

Sporulated, freshly, harvested leaves from *Phlebodium decumanum* are dried for 1 week in a drying room by introducing pressed air at 40–50° C. Once dried, the leaves are ground. A mixture of small particles and fine powder is obtained. 100 kg dry, ground leaves are extracted 3 times with 400 litters of 7/3 methyl alcohol/de-ionized water at 40° C. for 12 hours. Hydromethanolic extracts are collected and concentrated at 40° C. under reduced pressure until complete removal of the alcohol. The fine suspension obtained is treated 3 times with an equal volume of non-polar solvent, preferably petroleum ether or petroleum ether/dichoro.methane mixtures, in order to remove any residual lipids. The delipidated water soluble fraction is purified by passing it through an ion-exchange resin column followed by treatment with active charcoal, sodium metabisulfite and filtration. Concentration of the solution under reduced pressure, until a final water content of 20%, yields 5–10% (5–10 kg) of EXPLY-37.

TABLE 1

Composition of the purified, standardized water-soluble fraction from *Phlebodium decumanum* leaves (EXPLY-37).

| | % |
|---|---|
| Total solid content | 79.5–81.5 |
| Ash | 10–12 |
| Total N | 0.7–0.9 |
| Total protein | 4.9–5.9 |
| Lipids | <0.2 |
| Carbohydrates | 60.5–64.5 |
| pH | 5–5.1 |
| Refractive index | 1.4–1.5 |
| UV absorption | 235–237 nm |
| | 274–284 nm |
| Absorbance at 290 nm | 2.5–5 |

EXAMPLE 2

Preparation of Extracts from *Phlebodium decumanum* Rhizome 100 kg wet rhizomes, freshly harvested are successively extracted at 40° C., for 10 hours with:

a) 400 L methylalcohol
b) 400 L methylalcohol/water (8:2)
c) 400 L methylalcohol/water (7:3)

The different extracts are combined and concentrated at 40° C. and 25 mm until complete removal of the alcohol. The cloudy aqueous solution is extracted twice with methylene chloride or mixtures methylene chloride:petroleum ether.

The aqueous phase is then treated with active charcoal until a final absorbance of 0.5–1.5 at 290 nm is reached. Final concentration of the solution at 40° C. and 25 mm pressure gives a water-soluble fraction with a total solid content of 80%. A yield of 1–3 kg of purified and standardized rhizome extract is obtained. Its composition is batch to bath constant and reproducible within narrow limits (Table 2).

TABLE 2

Composition of the purifieds standardized water-soluble fraction from *Phlebodium decumanum* rhizomes

| | % |
|---|---|
| Total solid content | 80–81 |
| Ash | 10–12 |
| Total N | 0.6–0.7 |
| Total protein | 4–4.5 |
| Lipids | 0.5 |
| Carbohydrates | 65–66 |
| pH | 5–5.1 |
| Refractive index | 1.4–1.5 |
| UV absorption peaks at | 237 nm and 272 nm |
| Absorbance at 290 nm | 0.5–1.5 |

EXAMPLE 3

Capsules Containing EXPLY-37 and Rhizome 50 kg fresh rhizomes from *Phebodium decumanum*, freed from villosities, are washed by successive immersions in a dilute aqueous solution containing active chlorine, de-ionized water, absolute ethyl alcohol and sterile de-ionized water. The rhizomes are dried in a fluid layer dryer at 40°–50° C. for 2 hours. The dry rhizomes are ground and sieved. A fine powder is obtained.

7,5 Kg EXPLY-37 are added to 22.5 kg rhizome powder with stirring in a 100 L capacity stainless steel mixer. Stirring continues until a homogeneous mixture is obtained. The mixture is then dried on plates in the oven at 40–50° C. for 24 hours. The powder is sieved through a 18 mesh sieve. Capsules containing 300 mg powder are prepared.

EXAMPLE 4

Capsules Containing EXPLY-37 Enriched Powder

By following a process similar to that described in Example 3, the mixture is prepared with 25.5 Kg rhizome powder and 18.5 Kg EXPLY-37. After drying homogenizing and sieving, capsules containing 440 mg powder are prepared.

EXAMPLE 5

Capsulas Containing EXPLY-37, Rhizome and Rhizome Extract

By following a similar process to that described in Example 3, a final mixture containing 26.8 kg powdered dry rhizome, 10 kg EXPLY-37 and 3.2 kg rhizome extract is prepared. Capsules containing 400 mg dry powder are manufactured. The relative proportions [XPLY-37: rhizome extract] can vary within a wide range (50:50) to (95:5)

EXAMPLE 6

EXPLY-37 Syrup

A homogeneous mixture is made up of 7.8 kg of *Saccharum officinarum* liquid extract and 190 g glycyrrhiza glabra liquid extract by stirring in a stainless steel mixer tank provided of a paddle stirring element at 20 rpm. 10 g citric acid are then added, followed by 2 kg EXPLY-37. Stirring is continued at 37° C. until complete homogenization. A syrup containing 200 mg EXPLY-37 /g is obtained.

By using different amounts of EXPLY-37 and making the necessary corrections in the amounts of excipients, syrups containing 50–500 mg EXPLY-37/g are prepared.

EXAMPLE 7

Syrups Containing EXPLY-37 and Rhizome Extract

By following the steps described in Example 6, a syrup containing 1 kg EXPLY-37+1 kg rhizome extract is obtained. Final concentration: 200 mg whole extract/g.

Syrup having a composition in the range 50–500 mg total extract/g can be prepared in a similar way. The relative proportions [EXPLY-37: rhizome extract ] can vary from (50:50) to (95:5)

EXAMPLE 8

Syrups Containing EXPLY-37 and Rhizome Extract 5,000 g invert sugar, 2,500 g sorbitol and 50 g propylenglycol are successively added on 2,450 mL de-ionized water in a glass tank provided of anchor stirring element. When the mixture is fully homogenized, 2.5 Kg EXPLY-37 or 2 Kg EXPLY-37 and 0.5 Kg rhizome extract are added under slow stirring at temperature of 30°–40° C. Syrup concentration: 200 mg/ml, expressed as EXPLY-37 or EXPLY-37+rhizome extract].

Clinical Results

I. Patients with Advanced HIV Infection

The number of HIV infected patients is reaching dramatic levels in Central America and Caribbean countries. Honduras' case is known by the number of patients in advanced stager of the disease, the early age of many of these patients and the lack of resources for diagnosis, prevention and treatment of the disease with anti-retroviral drugs.

Honduran patients, knowing the existence of the lake Yojoa Polypodiacee cultures, requested some compassionate remedies for the improvement of their general condition. HIH decided to prepare different formulations to be supplied as nutritional and energetic supplements to those patients willing to use the remedy. Said formulations are within the scope of this patent application.

1. Dose exploration in individual patients

Preliminary results correspond to five advanced patients in very deteriorated conditions. No inclusion criteria were applied. These patients were given, together with the regular diet, EXPLY-37 syrup containing only EXPLY-37 and prepared as in Example 8. Daily doses were given thrice daily and ranged between 1 and 3 g/day. After the first month of treatment all five patients received 3 g/day. Results are summarised in table 3

TABLE 3

Results in isolated cases

| Patient | Age/sex | Appetite | Months of treatment | Body weight Quality of life |
|---|---|---|---|---|
| 1 | 52/M | 5+ | 9 | Body weight increase to normal figures. Professional activity became to normal at the 2$^{nd}$ month |
| 2 | 21/F | 4+ | 5 | Body weight increase to normal figures. Quality of life |
| 3 | 22/M | 4+ | 5 | Body weight increase to normal figures. Quality of life |
| 4 | 27/M | 3+ | 4 | 60% body-weight increase. Professional activity became to normal at the 1$^{st}$ month of treatment |
| 5* | 20/M | — | — | |

*This patient died two days after initiating the treatment. Appetite scale 1+ to 5+.

2. Groups of controlled patients

A first group of 5 patients was treated according to a simple protocol including the following criteria:

Age 18–35 years
Number of patients 10, both sexes
Inclusion criteria
   Advanced HIV infection
   Absence of opportunistic infection
   No treatment with anti-retroviral drugs
   CD4++ not lower than 400
   Body weight loss in the previous 6-month period not lower than 10%
Parameters to be measured
   Appetite recovery
   Body weight evolution
   Quality of life This group of patients is on the 2$^{nd}$ month of treatment. They are receiving as a nutritional supplement 3.1 g EXPLY-37 doses par day as a syrup prepared according to Example 8. Table 4 summarizer the results corresponding to the first 5 controlled patients.

TABLE 4

Results in groups of controlled patients

| Patient | Age/sex | Appetite | Months of treatment | Body weight Quality of life |
|---|---|---|---|---|
| 1 | 32/M | 3+ | 2 | Progressive body weight gain. Improvement in the quality of life |
| 2 | 33/F | 3+ | 2 | Id |
| 3 | 26/F | 3+ | 2 | Id |
| 4 | 27/M | 4+ | 2 | Id |
| 5 | 33/F | 3+ | 2 | Id |

The initial inclusion criteria were modified from patient no 6 on due to the difficulties in selecting patients with CD4+ count not lower than 400: most of the examined patients showed a CD4+ count between 100 and 200 and were suffering from different associated opportunistic infections.

A second group of patients meeting the new inclusion criteria are being treated with capsules containing [EXPLY-37 +rhizome] and prepared as in Example 4. The daily dose is 6–12 capsules/day. The first 4 patients showed a general improvement similar to that observed in the previous groups: rapid appetite gain, smooth and progressive body-weight gain, improvement in the quality of life and resumption of both personal and professional activities in those cases where these activities had been discontinued.

II. Treatment of Cancer Patients

Continuous use of different EXPLY-37 formulations in cancer patients with different type of tumors at different stages, either during conventional anticancer treatments or following to the application of such treatments has shown the efficacy of said formulations in:

reversion of cachexia and quality of life recovery in very ill patients.

application of new chemotherapy protocols in recovered patients.

maintenance of good general condition and quality of life in said patients.

reduction of the undesirable effects in patients under chemotherapy.

general condition and quality of life recovery following to the application of conventional anticancer treatments.

Experience has been accumulated for several years after the positive results obtained with the first patient.

Table 5 summarizes some representative cases where a relationship between the positive evolution in the patient condition is associated to the continuous use of EXPLY-37.

| Patient | Sex/Age | Pathology/date | Treatment | EXPLY-37 | Results 5/98 |
|---|---|---|---|---|---|
| 1 | M/60 | Colon neoplasia /1/94 | Surgery Chemotherapy in 1994 | 1–3 g/day starting 01/94. Alternatively formulations examples 5, 6, 7, 8 | Excellent tolerance to chemotherapy. Body weight gain. Excellent quality of life |
| 2 | M/58 | Colon neoplasia /02/97 | Surgery Chemotherapy | 2 g/day starting 2/97 Formulations as in example 6 | Progressive recovery of quality of life. Resuming the sport activity (hobby) 5/98 |
| 3 | F/49 | Breast carcinoma II 10/93 Liver metastasis 10/95 Bone metastasis 9/97 | Total mastectomia Surgery Chemotherapy (under way) | 2 g/day starting 9/97. Formulations example 4 ad 5 | Good tolerance to (CT) Good quality of life Favorable evolution of metastasis |
| 4 | F/51 | Breast carcinoma and liver metastasis /7/95 | Total mastectomia Chemotherapy cycles in 1996 | 1–2 g/day starting 01/97. Formulations as in example 6 | Body weight back to normal figures. Excellent quality of life. Metastasis in regression. |
| 5 | M/52 | Bladler neoplasia III 10/95 | Transuretral resection Mytomycin C instillations, radiotherapy, BCG (1996–1997) | 1–2/day starting 10/96. Formulations as in 4, 6, 7, | Very surprising and favorable evolution in 1997. Negative biopsies 9/97, 12/97 and 2/98. Excellent quality of life. |
| 6 | M/72 | Renal carcinoma 10/97 | CT initiated and discontinued due to anuria | 1–2/day starting 12/97. Formulation as in example 6 | Dramatic improvement Possible re-start of CT |
| 7 | F/38 | Renal carcinoma and bone metastasis 2/98 | Surgery CT | 2 g/day starting 4/97 Formulations as in Example 3, 4 | Appetite recovery Good tolerance to CT Good quality of life |
| 8 | M/62 | Acute myeloblastic leukemia 1/98 | CT | 3 p/day starting on 4/98. Formulations as in example 6 | Appetite and body-weight back to normal. Cachexia reversion. General improvement. |

What is claimed is:

1. A purified and standardized water-soluble extract obtained from the leaves of *Phlebodium decumanum*, said extract being commonly known as EXPLY-37, having the following characteristics:

|  | % by weight |
|---|---|
| Total solid content | 79.5–81.5 |
| Ash | 10–12 |
| Total N | 0.7–0.9 |
| Total Protein | 4.9–5.9 |
| Lipids | <0.2 |
| Carbohydrates | 60.5–64.5 |
| pH | 5–5.1 |
| Refractive index | 1.4–1.5 |
| UV absorption | 235–237 nm 274–284 nm |
| Absorbance at 290 nm | 2.5–5 |

2. A method for the preparation of the water-soluble extract according to claim 1 comprising the steps of:

(a) removing lipid from dry, ground, sporulated *Phlebodium decumanum* leaves by treatment with petroleum ether, methylene chloride or mixtures thereof to yield a delipidated water soluble fraction;

(b) extracting said water soluble fraction with a mixture of methyl alcohol and water, (c) removing methyl alcohol from said fraction at reduced pressure, (d) purifying the resultant water soluble fraction by treatment in a mixed ion exchange column containing active charcoal, sodium metabisulphite and filtration, and (e) concentrating the resultant purified water soluble fraction until a batch-to-batch constant and reproducible extract is obtained.

3. A method for the preparation of the water soluble extract according to claim 1 comprising the steps of:

(a) extracting dry, ground, sporulated *Phlebodium decumanum* leaves by treatment with a mixture of methyl alcohol and water to yield a water soluble fraction, (b) removing methyl alcohol from said fraction at reduced pressure, (c) removing lipids from said fraction with petroleum ether, methylene chloride or mixtures thereof, (d) purifying the delipidized fraction by passing it through a mixed ion exchange column including active charcoal and sodium metabisulphite and filtering the fraction, and (e) concentrating the resultant purified water soluble fraction until a batch-to-batch constant and reproducible extract is obtained.

4. A composition obtained according to the method of claim 2.

5. A composition obtained according to the method of claim 3.

6. A composition prepared according to claim 2 comprising from 50–750 mg of the water-soluble extract obtained from the leaves of *Phlebodium decumanum* in a soft gelatine capsule.

7. A composition prepared according to claim 2 further comprising from 50–750 mg of an extract of *Phlebodium decumanum* rhizome in a soft gelatine capsule.

8. The composition according to claim 7 wherein the ratio of EXPLY-37 to the extract of *Phlebodium decumanum* rhizome ranges from 50:50 to 95:5.

9. A composition prepared according to claim 2 further comprising ground, homogenized extract of *Phlebodium decumanum* rhizome, said composition being in the form of a dry powder in a hard gelatine capsule containing from 100–500 mg of said powder.

10. A composition according to claim 9 wherein the ratio of ground, homogenized *Phlebodium decumanum* rhizome to EXPLY-37 ranges from 4:1 to 1:1.

11. A composition prepared according to claim 2 further comprising ground, homogenized *Phlebodium decumanum* rhizome and an extract of *Phlebodium decumanum* rhizome, said composition being in the form of a dry powder in a hard gelatine capsule containing from 100–500 mg of said powder.

12. A composition according to claim 11 wherein the ratio of EXPLY-37 to said extract of *Phlebodium decumanum* rhizome ranges from 50:50 to 95:5.

13. A composition according to claim 11 of wherein the ratio of the mixture of EXPLY-37 and the extract of *Phlebodium decumanum* rhizome to ground, homogenized *Phlebodium decumanum* rhizome ranges from 4:1 to 1:1.

14. A composition prepared according to claim 2 further comprising excipients suitable for liquid preparations.

15. A composition prepared according to claim 2 further comprising a liquid extract of *Saccharum officinarum*, a liquid extract of *Glycyrrhiza glabra*, citric acid, inverted sugar, sorbitol, propylene glycol and mixtures thereof, said composition being in the form of a syrup having a concentration of EXPLY-37 ranging from 20–500 mg/ml.

16. The composition according to claim 14 further comprising an extract of *Phlebodium decumanum* rhizome, said composition being in the form of a syrup having an admixed concentration of EXPLY-37 and the extract of *Phlebodium decumanum* rhizome between 20–500 mg/ml.

17. The composition according to claim 16 wherein the ratio of EXPLY-37 to the extract of *Phlebodium decumanum* rhizome ranges from 50:50 to 95:5.

18. A nutritional supplement comprising a composition prepared in accordance with claim 2.

* * * * *